(12) United States Patent
Henkelmann et al.

(10) Patent No.: US 7,790,937 B2
(45) Date of Patent: Sep. 7, 2010

(54) PROCESS FOR THE PREPARATION OF 1,2-PROPANEDIOL

(75) Inventors: Jochem Henkelmann, Mannheim (DE); Michael Becker, Offenburg (DE); Jochen Buerkle, Mannheim (DE); Peter Wahl, Heidelberg (DE); Gerhard Theis, Maxdorf (DE); Stephen Maurer, Neustadt-Gimmeldingen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/281,406

(22) PCT Filed: Mar. 2, 2007

(86) PCT No.: PCT/EP2007/051983

§ 371 (c)(1),
(2), (4) Date: Sep. 2, 2008

(87) PCT Pub. No.: WO2007/099161

PCT Pub. Date: Sep. 7, 2007

(65) Prior Publication Data

US 2009/0216050 A1    Aug. 27, 2009

Related U.S. Application Data

(60) Provisional application No. 60/778,371, filed on Mar. 3, 2006.

(30) Foreign Application Priority Data

Mar. 3, 2006  (EP) .................................. 06004414

(51) Int. Cl.
*C07C 29/132* (2006.01)
(52) U.S. Cl. ..................................... 568/861
(58) Field of Classification Search .................. 568/861
See application file for complete search history.

(56) References Cited

U.S. PATENT DOCUMENTS

| 2,360,844 | A | 10/1944 | Bradshaw et al. |
| 4,297,247 | A | 10/1981 | Krabetz et al. |
| 5,354,878 | A | 10/1994 | Connemann et al. |
| 5,403,962 | A | 4/1995 | Schneider et al. |
| 5,536,694 | A | 7/1996 | Schuetz et al. |
| 5,616,817 | A | 4/1997 | Schuster et al. |
| 5,677,261 | A | 10/1997 | Tenten et al. |
| 6,121,188 | A | 9/2000 | Breitscheidel et al. |
| 2005/0204612 | A1 | 9/2005 | Connemann et al. |

FOREIGN PATENT DOCUMENTS

| CA | 2208720 C | 7/1996 |
| CA | 2570915 A1 | 1/2006 |
| DE | 524101 | 5/1931 |
| DE | 541362 | 1/1932 |
| DE | 2628987 A1 | 1/1978 |
| DE | 2909671 A1 | 10/1980 |
| DE | 4021230 A1 | 1/1991 |
| DE | 4028295 A1 | 3/1992 |
| DE | 4302464 A1 | 8/1994 |
| DE | 4335360 A1 | 4/1995 |
| DE | 4345265 A1 | 9/1995 |
| DE | 4446907 A1 | 7/1996 |
| DE | 10243700 A1 | 4/2004 |
| EP | 0434062 A1 | 6/1991 |
| EP | 0523015 A2 | 1/1993 |
| EP | 0552463 A1 | 7/1993 |
| EP | 0714700 A2 | 6/1996 |
| EP | 0842699 A2 | 5/1998 |
| GB | 1579159 | 11/1980 |
| WO | WO-2005/095536 A2 | 10/2005 |
| WO | WO-2006/005505 A1 | 1/2006 |

OTHER PUBLICATIONS

Dasari, M.A., et al., "Low-pressure hydrogenolysis of glycerol to propylene glycol," Applied Catalysis A: General, 2005, vol. 281, pp. 225-231.
Connor, R., et al., "Hydrogenolysis of oxygenated organic compounds," J. Am. Chem. Soc., 1932, vol. 54, pp. 4678-4690.
Chaminand, J., et al., "Glycerol hydrogenolysis on heterogeneous catalysts," Green Chem., 2004, vol. 6, pp. 359-361.
Montassier, C., et al., "Transformation de polyols par catalyse hétérogène en phase liquide sur les métauxe," Bulletin de la Societe Chimique de France, 1989, No. 2, pp. 148-155.

*Primary Examiner*—Sikarl A Witherspoon
(74) *Attorney, Agent, or Firm*—Connolly Bove Lodge & Hutz LLP

(57) ABSTRACT

The present invention relates to a process for the preparation of 1,2-propanediol, in which a glycerol-containing stream, in particular a stream obtained on an industrial scale in the production of biodiesel, is subjected to a hydrogenation.

16 Claims, No Drawings

PROCESS FOR THE PREPARATION OF 1,2-PROPANEDIOL

RELATED APPLICATIONS

This application is a national stage application (under 35 U.S.C. §371) of PCT/EP2007/051983, filed Mar. 2, 2007, which claims benefit of European Application No. 06004414.6, filed Mar. 3, 2006, and U.S. Provisional Application Ser. No. 60/778,371, filed Mar. 3, 2006.

The present invention relates to a process for the preparation of 1,2-propanediol, in which a glycerol-containing stream, in particular a stream obtained on an industrial scale in the preparation of biodiesel, is subjected to a hydrogenation.

Diminishing mineral oil reserves and increasing fuel prices are leading to a growing interest in the replacement of fuels produced on the basis of mineral oil by economical and environmentally friendly alternatives. Processes for the production of fuels from biogenic fat- or oil-containing starting mixtures and used oils obtained, for example, in restaurants and animal fats have long been known, rapeseed oil currently predominantly being used in Central Europe as a starting material in the production of biogenic fuels. Biogenic oils and fats themselves are less suitable as engine fuel since they have to be purified beforehand by generally complicated methods. These include the removal of lecithins, carbohydrates and proteins, the removal of the so-called oil sludge and the removal of the free fatty acids present in relatively large amounts, for example, in rapeseed oil. Vegetable oils treated in this manner nevertheless differ from the technical properties of conventional diesel fuels in several respects. Thus, they have as a rule a higher density than diesel fuel, the cetane number of rapeseed oil is lower than that of diesel fuel and the viscosity is several times higher compared with that of diesel fuel. This leads to an unacceptable deterioration in the fuel properties, such as to nonuniform running behavior of the engine, to substantially increased noise emission and, owing to the higher viscosity, to poorer atomization and combustion in the combustion chamber. In conventional engines, the use of pure vegetable oils therefore leads to coking, associated with increased particle emission. It is known that these problems can be solved by converting the triglycerides (fatty acid esters of glycerol) present in the biogenic oil and fat starting mixtures into monoalkyl esters of fatty acids, in particular methyl or ethyl esters. These esters, also referred to as "biodiesel", can as a rule be used in diesel engines without major retrofits, it often even being possible to reduce the emission of uncombusted hydrocarbons and soot particles in comparison with normal diesel fuel. The transesterification of the triglycerides for biodiesel production also results in glycerol (≈10%), which, for reasons of both cost-efficiency and sustainability, should be utilized. There is therefore a need for effective and economical processes which also permit utilization of the glycerol obtained in biodiesel production. These processes should in particular also be suitable for the utilization of further glycerol streams available on an industrial scale.

U.S. Pat. No. 2,360,844 describes a process for the preparation of soaps, in which a crude glyceride is transesterified with $C_1$-$C_4$-alkanols and the glycerol liberated is separated from the monoalkyl esters. The utilization of the glycerol obtained is not described.

U.S. Pat. No. 5,354,878 describes a process for the preparation of lower alkyl esters of higher fatty acids having a low residual glycerol content by transesterification of fatty acid triglycerides and the use of these esters as diesel fuel.

DE 102 43 700 A1 describes a pressureless process for the preparation of alkyl esters of higher fatty acids, in particular biodiesel, from fatty acid triglyceride starting mixtures comprising free fatty acids by a combination of acidic esterification and basic transesterification. The glycerol obtained in the transesterification is partly used as an entraining agent in the esterification of the free fatty acids.

It is known that alcohols having a relatively high hydricity can be converted into alcohols having a lower hydricity by catalytic hydrogenation. Thus, German Patent 524 101 describes such a process in which, inter alia, glycerol is subjected to a gas-phase hydrogenation in the presence of a hydrogenation catalyst with hydrogen in considerable excess. Specifically, copper or cobalt catalysts activated with Cr are used for the hydrogenation of glycerol.

German patent 541 362 describes a process for the hydrogenation of polyoxy compounds such as, for example, glycerol, in the presence of catalysts at elevated temperatures above 150° C. and under superatmospheric pressure. Specifically, the hydrogenation of glycerol using a nickel catalyst at a temperature from 200 to 240° C. and a hydrogen pressure of 100 atm is described.

R. Connor and H. Adkins, in J. Am. Chem. Soc. 54, 1932, pages 4678-4690, describe the hydrogenolysis of oxygen-containing organic compounds, inter alia of 98% strength glycerol, to 1,2-propanediol in the presence of a copper-chromium-barium oxide catalyst.

C. Montassier et al., in Bulletin de la Société Chimique de France 1989, No. 2, pages 148-155, describe investigations of the reaction mechanism of the catalytic hydrogenation of polyols in the presence of various metallic catalysts, such as, for example, of glycerol in the presence of Raney copper.

J. Chaminand et al., in Green Chem. 6, 2004, pages 359-361, describe the hydrogenation of aqueous glycerol solutions at 180° C. and 80 bar hydrogen pressure in the presence of supported metal catalysts based on Cu, Pd and Rh.

DE 43 02 464 A1 describes a process for the preparation of 1,2-propanediol by hydrogenation of glycerol in the presence of a heterogeneous catalyst at pressures of from 20 to 300 bar, in particular at from 100 to 250 bar, and temperatures of from 150° C. to 320° C., glycerol in vapor or liquid form being passed over a catalyst bed. Inter alia, copper chromite, copper zinc oxide, copper aluminum oxide and copper silicon dioxide are mentioned as catalysts. The use of glycerol-containing streams from biodiesel production and measures for the pretreatment of such streams before their use for the hydrogenation are not described in this document.

EP 0 523 015 describes a process for the catalytic hydrogenation of glycerol for the preparation of 1,2-propanediol and 1,2-ethanediol in the presence of a Cu/Zn catalyst at a temperature of at least 200° C. In this process, the glycerol is used as an aqueous solution having a glycerol content of from 20 to 60% by weight, the maximum glycerol content in the working examples being 40% by weight.

WO 2005/095536 describes a low-pressure process for converting glycerol into propylene glycol, in which a glycerol-containing stream having a water content of not more than 50% by weight is subjected to a catalytic hydrogenation at a temperature in the range of from 150 to 250° C. and a pressure in the range of from 1 to 25 bar.

M. A. Dasari et al., in Appl. Chem. A: General 281, 2005, pages 225-231, describe a process for the low-pressure hydrogenation of glycerol to propylene glycol at a temperature of 200° C. and a hydrogen pressure of 200 psi (13.79 bar) in the presence of a nickel, palladium, platinum, copper or copper chromite catalyst. Different reaction parameters were tested, such as, inter alia, the water content of the glycerol used. It was found that, although the conversion increased with decreasing water content, the highest selectivity was achieved in this low-pressure process at a water content of 20% by weight.

U.S. Pat. No. 5,616,817 describes a process for the preparation of 1,2-propanediol by catalytic hydrogenation of glycerol at elevated temperature and superatmospheric pressure, in which glycerol having a water content of not more than 20% by weight is reacted in the presence of a catalyst which comprises from 40 to 70% by weight of cobalt, if appropriate, manganese and/or molybdenum and a low copper content of from 10 to 20% by weight. The temperature is in the range of from about 180 to 270° C. and the pressure in a range of from 100 to 700 bar, preferably from 200 to 325 bar.

It is the object of the present invention to provide a process for the preparation of 1,2-propanediol which permits the hydrogenation of glycerol-containing streams with high selectivity and/or low energy consumption, as required, for example, for separating off water. The process should be suitable in particular for the further processing of glycerol streams obtained on an industrial scale, such as those obtained in the transesterification of fatty acid triglycerides for the preparation of alkyl esters of higher fatty acids.

The invention therefore relates to a process for the preparation of 1,2-propanediol, in which
a) a glycerol-containing stream is provided and
b) the glycerol-containing stream is subjected to a hydrogenation in the presence of a copper-containing, heterogeneous catalyst at a temperature of from 100 to 320° C. and a pressure of from 100 to 325 bar.

The hydrogenation product obtained in step b) can, if appropriate, be subjected to at least one working-up step (step c)).

In principle, all glycerol-containing streams, including those from processes carried out industrially and having the purities resulting there, are suitable for use in the process according to the invention. These include in particular glycerol-containing streams from the processing of oil- and/or fat-containing starting materials, for example from soap production, fatty acid and fatty acid ester production, etc. The glycerol-containing stream provided in step a) is preferably a glycerol-containing stream obtained in the preparation of alkyl esters of higher fatty acids by transesterification of fatty acid triglycerides, as obtained in particular in the production of "biodiesel". This embodiment of the process according to the invention is described in more detail below.

The glycerol-containing stream used in step a) preferably has a water content of not more than 30% by weight, preferably of not more than 20% by weight. A water content corresponding to glyceryl monohydrate (water content 16.3% by weight) or less is particularly preferred. In a special embodiment, a glycerol-containing stream which is substantially anhydrous is used. In the context of the present invention, "substantially anhydrous" is understood as meaning a water content of not more than 3% by weight, particularly preferably of not more than 1% by weight. The use of glycerol-containing streams having a water content in the range of up to 30% by weight, in particular up to 20% by weight, permits the preparation of 1,2-propanediol in high yields and with high selectivity in the temperature and pressure range used for the hydrogenation. The hydrogenation of glycerol-containing streams which are not substantially anhydrous and in particular of streams which have a higher water content than glyceryl monohydrate, is likewise possible in high yields and with high selectivities but, owing to the reduced space-time yield, is less economical. Nevertheless, a water content in the range of from 3 to 30% by weight may be advantageous for the rheological properties during the hydrogenation. A special embodiment of the process according to the invention therefore relates to the use of glycerol-containing streams having a water content in the range of from 3 to 30% by weight, preferably from 5 to 20% by weight, for reducing the viscosity during the hydrogenation.

The glycerol-containing streams may have at least one further, preferably glycerol-miscible (and hence as a rule also water-miscible), organic solvent instead of or in addition to water. The glycerol-containing streams provided in step a) preferably have a total solvent content of not more than 20% by weight, particularly preferably not more than 15% by weight, in particular not more than 10% by weight and especially not more than 5% by weight. If solvent mixtures which comprise water and at least one glycerol- or water-miscible organic solvent are used, the proportion of the organic solvent is preferably not more than 50% by weight, particularly preferably not more than 20% by weight, based on the total weight of the solvent. Suitable glycerol-miscible organic solvents are $C_1$-$C_4$-alkanols, such as methanol, ethanol, n-propanol, isopropanol, n-butanol, tert-butanol, polyols and mono- and dialkyl ethers thereof, cyclic ethers, such as dioxane and tetrahydrofuran, etc. Other suitable solvents are aromatic hydrocarbons, such as benzene, toluene or the xylenes. Preferred organic solvents are $C_1$-$C_4$-alkanols, in particular methanol and/or ethanol, and mixtures thereof with water. However, the glycerol-containing streams used in step a) preferably have no organic solvents.

The glycerol-containing streams provided in step a) may be subjected to at least one working-up step. This includes, for example, at least one purification step for removing undesired components. This furthermore includes a reduction of the content of water and/or, if present, organic solvents.

Depending on the origin, the glycerol-containing streams may also comprise inorganic salts as undesired components. These can be removed from the crude glycerol by the working-up processes described below. Thermal working-up (for example with the use of a Sambay evaporator) is particularly suitable for this purpose.

Depending on the origin, the glycerol-containing streams may also comprise catalyst poisons, i.e. components which adversely affect the hydrogenation by deactivating the hydrogenation catalyst. These include, for example, nitrogen-containing compounds, such as amines, and sulfur-containing compounds, such as sulfuric acid, hydrogen-sulfide, thioalcohols, thioethers, e.g. dimethyl sulfide and dimethyl disulfide, carbon oxide sulfide, amino acids, e.g. amino acids comprising sulfur and additional nitrogen groups, fatty acids and salts thereof etc. The catalyst poisons furthermore include halogen compounds, traces of conventional extracting agents, e.g. acetonitrile or N-methylpyrrolidone, etc. and, if appropriate, organic phosphorus and arsenic compounds. A catalyst poison frequently present in glycerol-containing streams from oil and fat refining is sulfuric acid, which is used as a catalyst in the esterification or transesterification.

For example, thermal working-up, preferably distillation, adsorption, ion exchange, a membrane separation method, crystallization or extraction or a combination of two or more of these methods can be used for working up the glycerol-containing streams in step a). Membrane separation methods with the use of membranes of defined pore sizes are especially suitable for reducing the water content and/or for salt removal. Crystallization is also understood as meaning the partial freezing of the glycerol-containing streams on cooled surfaces. Thus, it is possible to remove impurities which accumulate in the solid phase.

In a first embodiment, the glycerol-containing stream in step a) is subjected to a distillation for reducing the water content and/or for removing components which adversely affect the catalytic hydrogenation. This can in principle be effected by conventional distillation methods known to the person skilled in the art. Suitable apparatuses for the distillative working-up comprise distillation columns, such as tray columns, which may be equipped with caps, sieve plates, sieve trays, stacked packings, dumped packings, valves, side take-offs, etc., evaporators, such as thin-film evaporators, falling-film evaporators, forced-circulation evaporators, Sambay evaporators, etc., and combinations thereof. The removal of sulfuric acid takes place even as a result of a simple distillation, in particular a short path distillation.

Suitable separation processes are described in the following documents: Sattler, Klaus: Thermische Trennverfahren, $3^{rd}$ edition, Wiley VCH, 2001; Schlünder E. U., Thurner F.: Destillation, Absorption, Extraktion, Springer Verlag, 1995; Mersmann, Alfons: Thermische Verfahrenstechnik, Springer Verlag, 1980; Grassmann P., Widmer F.: Einführung in die thermische Verfahrenstechnik, de Gruyter, 1997; Weiβ S., Militzer K.-E., Gramlich K.: Thermische Verfahrenstechnik, Dt. Verlag für Grundstoffindustrie, Leipzig, Stuttgart, 1993. Reference is made here to these documents.

In a further embodiment, the glycerol-containing stream in step a) is subjected to a catalytic desulfurization, if appropriate in the presence of hydrogen, for reducing the contents of sulfur-containing compounds, especially sulfur-containing aromatic compounds. Suitable desulfurization agents comprise a metal component, wherein the metals are preferably selected from metals of groups 6, 7, 8, 9, 10, 11 and 12 of the periodic table of the elements. The metals are selected in particular from Mo, Ni, Cu, Ag, Zn and combinations thereof. Further suitable components of the desulfurization agents are doping agents. The metal component can be employed in oxidized form, reduced form and in form of a mixture that comprises oxidized and reduced constituents. The active components of the desulfurization agents (metal component(s) and optionally doping agent(s)) can be applied on a supporting material. Suitable supports are in principal the adsorbents and the catalyst supports mentioned in the following. Preferably, the supporting material is selected from active carbons, graphites, carbon black, $Al_2O_3$, $SiO_2$, $TiO_2$, $ZrO_2$, SiC, silicates, zeolithes, argillaceous earth (e.g. bentonite) and combinations thereof. The application of at least one metal component and optionally further components to a supporting material can be carried out by methods known to a person skilled in the art, e.g. by (co)-precipitation or impregnation. The desulfurization agents may be present in form of a geometric body, e.g. in form of spheres, rings, cylinders, cubes, cuboids or other geometric bodies. Unsupported desulfurization agents can be shaped by customary shaping processes, e.g. by extruding, tabletting, etc. The form of supported desulfurization agents is determined by the shape of the support. The desulfurization agents can be employed e.g. in the form of pressed cylinders, tablets, lozenges, wagon wheels, rings, stars or extrudates, such as solid extrudates, polylobal extrudates (e.g. trilobal), hollow extrudates and honeycomb bodies. A preferred desulfurization agent which comprises copper and zinc in an atomic ratio of from 1:0.3 to 1:10, preferably from 1:0.5 to 1:3, in particular from 1:0.7 to 1:1.5, is preferably used for the catalytic desulfurization. A desulfurization agent which comprises from 35 to 45% by weight of copper oxide, from 35 to 45% by weight of zinc oxide and from 10 to 30% by weight of alumina is preferably used. In a special embodiment, the desulfurization agent is a component capable of use as a hydrogenation catalyst in step b). In this respect, reference is made to the following disclosure of hydrogenation catalysts of the above mentioned composition and processes for their preparation.

In one configuration of this process variant, the glycerol-containing streams are brought into contact in at least one desulfurization zone with the desulfurization agent and then hydrogenated in at least one reaction zone.

It is self-evident to the person skilled in the art that the specific configuration and arrangement of the desulfurization and reaction zone(s) can be effected in any known manner. It is possible to arrange the desulfurization and reaction zone(s) spatially separate from one another, i.e. to separate them structurally from one another by the configuration of the apparatus or to realize them in one or more common desulfurization/hydrogenation zone(s).

The copper-zinc desulfurization agent can be obtained, for example, by a conventional precipitation or coprecipitation method and used in oxidized as well as in reduced form.

In a particular embodiment, the copper-zinc desulfurization agent comprises at least copper, zinc and aluminum, the copper:zinc:aluminum atomic ratio being in the range of from 1:0.3:0.05 to 1:10:2, preferably from 1:0.6:0.3 to 1:3:1 and in particular from 1:0.7:0.5 to 1:1.5:0.9.

For conversion into the reduced form, it is possible to subject the desulfurization agent to a hydrogen reduction. This is carried out at from about 150 to 350° C., preferably from about 150 to 250° C., in the presence of hydrogen, the hydrogen being diluted by an inert gas, such as, for example, nitrogen, argon, or methane, in particular nitrogen, so that the hydrogen content is 10% by volume or less, preferably 6% by volume or less, in particular from 0.5 to 4% by volume. The copper-zinc desulfurization agent thus obtained ("reduced form") can be used in this form in the desulfurization.

In an embodiment, the desulfurization of the glycerol-containing stream is carried out over the copper-zinc desulfurization agent in oxidized form without addition of hydrogen.

In a further embodiment, the desulfurization of the glycerol-containing stream is carried out over the copper-zinc desulfurization agent in oxidized form in the presence of hydrogen.

In a further embodiment, the desulfurization of the glycerol-containing stream is carried out over the copper-zinc desulfurization agent in reduced form without addition of hydrogen.

In a further embodiment, the desulfurization of the glycerol-containing stream is carried out over the copper-zinc desulfurization agent in reduced form in the presence of hydrogen.

Usually, the desulfurization is carried out in a temperature range of from 40 to 200° C., in particular at from 50 to 180° C., especially at from 60 to 160° C., preferably at from 70 to 120° C., at a pressure of from 1 to 40 bar, in particular at from 1 to 32 bar, preferably at from 1.5 to 5 bar, especially at from 2.0 to 4.5 bar. The desulfurization can be carried out in the presence of inert gases, such as, for example, nitrogen, argon or methane. As a rule, however, the desulfurization is carried out without addition of inert gases.

Usually—if desired—hydrogen having a purity of $\geq 99.8\%$ by volume, in particular of $\geq 99.9\%$ by volume, preferably of $\geq 99.95\%$ by volume, is used here. These purities apply analogously to the hydrogen which is used in the catalyst activations carried out if appropriate.

Usually, the weight ratio of glycerol-containing stream to hydrogen is in the range of from 40 000:1 to 1000:1, particularly in the range of from 38 000:1 to 5000:1, in particular in the range of from 37 000:1 to 15 000:1, preferably in the range of from 36 000:1 to 25 000:1, especially in the range of from 35 000:1 to 30 000:1.

The glycerol-containing stream thus desulfurized generally has a content of sulfur-containing impurities, especially of aromatic sulfur compounds of not more than 70 ppb, preferably of not more than 50 ppb and the total sulfur content is $\leq 200$ ppb, preferably $\leq 150$ ppb, in particular $\leq 100$ ppb altogether.

The desulfurization agents described above also make it possible to reduce or to remove chlorine, arsenic and/or phosphorus or corresponding chlorine, arsenic- and/or phosphorus-containing compounds from the aromatic hydrocarbon or from the mixture of aromatic hydrocarbons.

In a further embodiment, the glycerol-containing stream in step a) is brought into contact with at least one adsorbent for removing components which adversely affect the catalytic hydrogenation.

The adsorbents generally have a specific surface area, determined according to BET, in the range of from about 10 to 2000 $m^2/g$, preferably in the range of from 10 to 1500 $m^2/g$, more preferably in the range of from 10 to 400 $m^2/g$, especially in the range of from 60 to 250 $m^2/g$.

Suitable adsorbents are, for example, active aluminas. They are prepared, for example, starting from aluminum hydroxide, which is obtainable from aluminum salt solutions by conventional precipitation methods. Active aluminas suitable for the process according to the invention are also obtainable starting from aluminum hydroxide gels. For the preparation of such gels, for example, precipitated aluminum hydroxide can be activated by conventional working-up steps, such as filtration, washing and drying, and then, if appropriate, milled or agglomerated. If desired, the resulting alumina can then also be subjected to a shaping method, such as extrusion, granulation, tabletting, etc. Suitable adsorbents are preferably the Selexsorb™ types from Alcoa.

Suitable adsorbents are furthermore alumina-containing solids. These include, for example, the so-called clays, which likewise have aluminas as the main constituent.

Other suitable adsorbents are aluminum phosphates.

Other suitable adsorbents are silicas, which are obtainable, for example, by dehydration and activation of silica gels. A further process for the preparation of silica is the flame hydrolysis of silicon tetrachloride, it being possible to vary the desired surface properties of the resulting silica in wide ranges by suitable variations of the reaction parameters, such as, for example, of the stoichiometric composition of the starting mixture and of the temperature.

Other suitable adsorbents are kieselguhrs, which likewise have silicas as the main constituent. These include, for example, the diatomaceous earth obtained from silicic sediments.

Other suitable adsorbents are titanium dioxides and zirconium dioxides, as described, for example, in Römpp, Chemie-Lexikon, $9^{th}$ edition (paperback), vol. 6, page 4629 et seq. and page 5156 et seq. and the literature cited there. Reference is made here to these in their entirety.

Other suitable adsorbents are phosphates, in particular condensed phosphates, such as, for example, fused or calcined phosphates, which have a large active surface area. Suitable phosphates are described, for example, in Römpp, Chemie-Lexikon, $9^{th}$ edition (paperback) vol. 4, page 3376 et seq. and the literature cited there. Reference is made here to this in its entirety.

Other suitable adsorbents are carbon-containing adsorbents, preferably active carbon. Active carbon is understood here in general as meaning carbon having a porous structure and large internal surface area. For the preparation of active carbon, vegetable, animal and/or mineral carbon-containing raw materials are heated, for example, with dehydrating agents, such as zinc chloride or phosphoric acid, or are carbonized by dry distillation and then oxidatively activated. For this purpose, for example, the carbonized material can be treated at elevated temperatures of from about 700 to 1000° C. with steam, carbon dioxide and/or mixtures thereof.

Use of ion exchangers and/or adsorber resins is also possible.

The adsorbents are preferably selected from titanium dioxides, zirconium dioxides, silicas, kieselguhr, aluminas, alumina-containing solids, aluminum phosphates, natural and synthetic aluminum silicates, phosphates, carbon-containing adsorbents and mixtures thereof.

The adsorbents generally have a specific surface area, determined according to BET, in the range of from about 10 to 2000 $m^2/g$, in particular in the range of from 10 to 1500 $m^2/g$ and especially in the range of from 20 to 600 $m^2/g$.

For the adsorptive removal of undesired components, in particular of components which adversely affect the catalytic hydrogenation, the glycerol-containing stream in step a) is brought into contact with at least one adsorbent in an adsorption zone.

In a special embodiment, an adsorbent which comprises at least one component also capable of use as a hydrogenation catalyst in step b) is used. The hydrogenation catalysts described in more detail below are referred to here in their entirety. Combinations of two or more than two adsorbents are also suitable for use as adsorbents. It is possible to use either exclusively components also capable of being hydrogenation catalysts, exclusively adsorbents not suitable as hydrogenation catalysts or combinations thereof.

In a preferred embodiment, the same component is used as adsorbent and as hydrogenation catalyst. If appropriate, one or more further, conventional adsorbents, as described above, differing from the hydrogenation catalyst, are additionally used here.

In a configuration of the process, glycerol-containing streams are brought into contact in at least one adsorption zone with the adsorbent and then hydrogenated in at least one reaction zone.

It is self-evident to the person skilled in the art that the specific configuration and arrangement of the adsorption and reaction zone(s) can be effected in any known manner. It is preferably to arrange the adsorption and reaction zone(s) spatially separate from one another, i.e. to separate them structurally from one another by the configuration of the apparatus.

If different adsorbents are used, for example, a first adsorption zone which comprises a first adsorbent can be provided in a first adsorption zone in a first reactor and separately, i.e. structurally separate therefrom, for example in a second reactor, a second adsorption zone which comprises a second adsorbent. Here, the first and/or the second adsorbent may comprise at least one component capable of use of a hydrogenation catalyst.

In a further embodiment, a conventional adsorbent is used together with an adsorbent capable of hydrogenation in a single adsorption zone, for example, in stratified form, mixed in the form of a random distribution or in the form of a gradient bed. The use in mixed form permits, if appropriate, better control of the temperature. In the case of a gradient bed, linear and non-linear gradients can be used. It may be advantageous here to implement the distribution within the bed in such a way that the glycerol-containing stream to be hydrogenated is first brought into contact with the conventional adsorbent before it is brought into contact with the adsorbent capable of hydrogenation.

Advantageously, at least two adsorption zones will be arranged in such a way that the glycerol-containing stream to be hydrogenated is brought into contact with a conventional adsorbent in the first adsorption zone and is brought into contact, in the second adsorption zone, with an adsorbent which comprises at least one component capable of use as a hydrogenation catalyst.

The glycerol-containing streams provided in step a) of the process according to the invention preferably originate from the production of biodiesel. In the context of the present invention, "biodiesel" is understood as meaning a mixture of fatty acid monoalkyl esters which can be obtained from biogenic oil- and/or fat-containing starting mixtures and can be used as fuel in diesel engines.

In principle, all available biogenic oil- and/or fat-containing starting mixtures are suitable for providing the glycerol-containing stream. Oils and fats are generally solid, semisolid or liquid fatty acid triglycerides, in particular from vegetable and animal sources, which chemically substantially comprise glyceryl esters of higher fatty acids. Suitable higher fatty acids are saturated or mono- or polyunsaturated fatty acids having preferably 8 to 40, particularly preferably 12 to 30, carbon atoms. These include, for example, n-nonanoic acid, n-decanoic acid, n-undecanoic acid, n-tridecanoic acid, myristic acid, pentadecanoic acid, palmitic acid, margaric acid, nonadecanoic acid, arachidic acid, behenic acid, lignoceric acid, cerotic acid, melissic acid, palmitoleic acid, oleic acid, linoleic acid, linolenic acid, stearic acid, elaostearic acid, etc.

Vegetable fats and oils are substantially based on fatty acids having an even number of carbon atoms, whereas animal fats and oils may also comprise fatty acids having an odd number of carbon atoms, in free form or bound as triglyceride esters. The unsaturated fatty acids occurring in vegetable fats and oils are present in the cis form, while animal fatty acids frequently have a trans configuration.

In principle, used or unused, unpurified or purified vegetable, animal or industrial oils or fats or mixtures thereof can be used for providing the glycerol-containing stream in step a). These may comprise proportions of further ingredients, for example free fatty acids. The proportion of free fatty acids is in general from 0% to 50%, e.g. from 0.1 to 20%, of the starting mixture used for the transesterification of the fatty acid triglycerides. Free fatty acids can, if desired, be removed before or after the transesterification of the fatty acid triglycerides. Salts of these fatty acids (for example the alkali metal salts) can be converted into the free acid beforehand by acidification with a strong acid, e.g. HCl. The isolation of the free fatty acids is effected, for example, by centrifuging. Preferably, the free fatty acids present in the starting mixture are likewise converted into the alkyl esters. This can be effected before, during or after the transesterification of the fatty acid triglycerides.

Used fats and oils suitable for providing the glycerol-containing stream in step a) are fat- and/or oil-containing components which, after their recovery from appropriate biogenic starting materials were first used for other purposes, for example for technical purposes or purposes for food production, and may be chemically modified or unmodified as a result of this use or may have additional ingredients which in particular are associated with this use. These can, if desired, be at least partly removed by transesterification before the use for providing the glycerol-containing stream. Unused fats and oils suitable for providing the glycerol-containing stream in step a) are fat- or oil-containing components which still have not been used for any other purpose after their recovery from the appropriate vegetable or animal starting materials and which therefore have only ingredients which originate from the starting materials or are associated with the recovery from the starting materials. Ingredients other than fatty acid triglycerides (and, if appropriate, free fatty acids) can, if desired, also be at least partially removed from these starting materials by transesterification before the use for providing the glycerol-containing stream.

For the purification and/or enrichment, the unused or used fats or oils can be subjected to removal of undesired ingredients, such as lecithins, carbohydrates, proteins, oil sludge, water, etc.

Vegetable oils and fats are those which originate predominantly from vegetable starting materials, such as seeds, roots, leaves or other suitable plant parts. Animal fats or oils originate predominantly from animal starting materials, such as animal organs, tissues or other body parts or body fluids, such as milk. Industrial oils and fats are those which were obtained in particular from animal or vegetable starting materials and treated for technical purposes. The used or unused, unpurified or purified oils and/or fats used according to the invention are selected in particular from the group consisting of soapstock, brown grease, yellow grease, industrial tallow, industrial lard, frying oils, animal fat, edible tallow, crude vegetable oils, crude animal oils or fats or mixtures thereof.

"Soapstock" is understood as meaning a byproduct obtained in the processing of vegetable oils, in particular a byproduct of edible oil refineries which is based on soybean, colza or sunflower oil. Soapstock has a proportion of from about 50% to 80% of free fatty acids.

"Brown grease" is understood as meaning an animal fat-containing waste product which has a proportion of from more than 15% to 40% of free fatty acids. "Yellow grease" comprises from about 5% to 15% of free fatty acids.

"Industrial tallow" and "industrial lard" are understood as meaning animal fats which are produced for industrial purposes and are obtained after the drying or wet melting process, for example from slaughter wastes. Industrial tallows are rated and handled according to their acid number, the content of free fatty acids being, for example, between 1 and 15 to 20% by weight and in some cases even higher, depending on origin.

The "animal fats" include in particular fat-containing waste products obtained in the utilization of poultry, cattle, pig, fish and marine mammal bodies, for example solar stearin, a solid residue which remains after lard oil has been forced out of pork lard.

The glycerol-containing stream in step a) is preferably provided from crude vegetable oils as starting material. It is possible to start from unpurified crude vegetable oils, i.e. from liquid or solid compositions which are obtained from vegetable starting materials, for example by pressing, these having undergone no other treatment than settling in generally customary periods and centrifuging or filtering, in which only mechanical forces, such as gravitational force, centrifugal force or pressure, are used for separating the oil from solid constituents. Such unpurified crude vegetable oils may also be vegetable oils obtained by extraction if the properties thereof do not differ, or differ only insignificantly, from the corresponding vegetable oils obtained by means of pressing. The proportion of free fatty acids in unpurified vegetable fats and oil differs and is, for example, from about 0 to 20%, such as, for example from 0.1 to 15%.

Before they are used for the transesterification, the vegetable oils can of course be subjected to one or more working-up steps, as described in more detail below. Thus, purified vegetable oils, for example raffinates or semiraffinates, of the abovementioned vegetable oils may also be used as starting materials.

A vegetable oil or fat which is preferably selected from rapeseed oil, palm oil, colza oil, soybean oil, sunflower oil, corn oil, cottonseed oil, palm kernel and coconut fat and mixtures thereof is preferably used for providing the glycerol-containing stream in step a). Particularly preferably used are rapeseed oil or a mixture containing rapeseed-oil.

Animal oil or fat which is preferably selected from milk fat, wool fat, beef tallow, pork lard, fish oils, blubber, etc. and mixtures thereof is also suitable for providing the glycerol-containing stream in step a). Before they are used for the transesterification, these animal fats or oils, too can be subjected to one or more working-up steps, as described in more detail below.

Preferably, the provision of the glycerol-containing stream in step a) comprises the following steps:

a1) provision of a biogenic fat- and/or oil-containing starting mixture, a2) transesterification of the fatty acid triglycerides present in the starting mixture with at least one $C_1$-$C_9$-monoalcohol and, if appropriate, esterification of the free fatty acids present in the starting mixture with formation of an esterification mixture, a3) separation of the esterification mixture to obtain at least one fraction enriched with biodiesel and at least one fraction enriched with glycerol liberated in the esterification, a4) if appropriate, purification of the fraction enriched with glycerol.

Step a1)

In a preferred embodiment, the provision of the biogenic fat- and/or oil-containing starting mixture in step a1) comprises at least one purification step. For the purification, the fat- and/or oil-containing starting mixture can be subjected to at least one purification process usually used for fats and oils, such as clarification, filtration, treatment with bleaching earths or treatment with acids or alkali for separating off troublesome impurities, such as proteins, phosphatides and slimes, and a combination of at least two of these purification steps.

Step a2)

At least one $C_1$-$C_9$-monoalcohol, in particular at least one $C_1$-$C_4$-monoalcohol is preferably used for the transesterification of the fatty acid triglycerides. The use of methanol or ethanol is preferred.

The transesterification of the fatty acid triglyceride can be effected by acidic or preferably basic catalysis. Suitable acids are, for example, mineral acids, such as HCl, $H_2SO_4$ or $H_3PO_4$.

At least one base is preferably used as the catalyst. Said base is preferably selected from alkali metal hydroxides, such as NaOH and KOH, alkaline earth metal hydroxides, such as $Ca(OH)_2$, alkali and alkaline earth metal $C_1$-$C_6$-alkanolates, such as $NaOCH_3$, $KOCH_3$, $Na(OCH_2CH_2)$ and $Ca(OCH_2CH_2)_2$ and mixtures thereof. NaOH, KOH or $NaOCH_3$ is particularly preferably used, very particularly preferably $NaOCH_3$.

The amount of base used is usually in the range of from 0.1 to 10% by weight, in particular from 0.2 to 5% by weight, based on the amount of fatty acid triglycerides used.

The base is preferably used in the form of an aqueous or alcoholic, particularly preferably alcoholic, solution. The solvent already used for the alcoholysis of the triglycerides is advantageously used as a solvent for the base. $NaOCH_3$ solution in methanol is preferably used for the transesterification.

The transesterification is preferably effected at a temperature from about 20 to 150° C., in particular from 30 to 95° C.

The transesterification is effected in apparatuses customary for this purpose and known to the person skilled in the art. In a suitable embodiment, the transesterification is effected continuously. The transesterification is preferably effected in at least one column, the transesterification mixture obtained simultaneously being subjected to a separation. In general, a higher-boiling phase which with enriched with the basic catalyst, with unconverted monoalcohol and with the glycerol formed in the transesterification is obtained and a lower-boiling phase which is enriched with the transesterification product is obtained. If the transesterification product still contains triglycerides which have not undergone transesterification, these can also be separated off and subjected to a further transesterification in the first or a further transesterification stage.

The last transesterification mixture is then transferred to a drying unit, residual amounts of water again being removed. After the drying in the drying apparatus, the desired end product biodiesel is present in purified form and can be used directly as fuel.

If the fat- and/or oil-containing starting mixture used for providing the glycerol-containing stream in step a) comprises free fatty acids, these can preferably be subjected to an esterification for conversion into esters suitable for biodiesel.

The free fatty acids are preferably transesterified with the same $C_1$-$C_9$-monoalcohol which was used for the transesterification of the fatty acid triglycerides. The esterification of free fatty acids can be effected before, during or after the transesterification of the fatty acid triglycerides. In a preferred embodiment the esterification of free fatty acids is effected before the transesterification of the fatty acid triglycerides.

The esterification of the free fatty acids can be effected by basic or preferably acidic catalysis. Suitable acids are the abovementioned mineral acids, such as HCl, $H_2SO_4$ or $H_3PO_4$, p-toluene sulfonic acid, etc. The esterification is preferably effected at a temperature of from about 20 to 95° C., in particular from 40 to 80° C.

The esterification is effected in apparatuses customary for this purpose and known to the person skilled in the art. These include stirred vessels and/or columns which, if desired, are connected to form cascades. The esterification of the free fatty acids is preferably effected in at least one esterification apparatus designed as a column, the esterification mixture obtained simultaneously being subjected to a separation. In a suitable embodiment, the esterification is effected in the presence of an entraining agent for facilitating the separation.

Step a3)

During or after the transesterification and/or esterification, the esterification mixture is subjected to a separation to obtain at least one fraction enriched with $C_1$-$C_9$-monoalcohol esters and at least one fraction enriched with glycerol liberated in the transesterification. The separation is preferably effected by conventional distillation methods known to the person skilled in the art. Suitable distillation apparatuses are those mentioned above.

Step a4)

The fraction obtained after separation of the esterification mixture in step a3) and enriched with glycerol can, if appropriate, be subjected to at least one working-up step. This includes, for example, the removal of undesired components, such as salts, and of components which adversely affect the catalytic hydrogenation or the removal of water and, if present, organic solvent. Reference is made to the above statements on these working-up steps, in their entirety.

The catalysts used in the process according to the invention may be unsupported catalysts or supported catalysts. They can be used in form of uniform-composition catalysts, impregnated catalysts, coated catalyst and precipitated catalysts.

In principle, a large number of copper-containing catalysts which may additionally comprise at least one further element of main group I, II or III, IV, V, or sub group I, II, IV, V, VI, VII, or VIII and of the lanthanides (IUPAC: groups 1 to 15 and the lanthanides) are suitable, in particular Ca, Mg, Al, La, Ti, Zr, Cr, Mo, W, Mn, Ni, Co, Zn and combinations thereof.

A special embodiment of catalysts which are particularly advantageous for use in the process according to the invention comprises skeletal or metal sponge catalysts, such as those referred to as "Raney catalysts". These include in particular Raney copper and copper-containing metal alloys in the form of a Raney catalyst. Raney catalysts whose metal component comprises at least 95%, in particular at least 99%, of copper are preferred. Processes for the preparation of Raney catalysts are known to the person skilled in the art and are described, for example, in DE-A-43 35 360, DE-A-43 45 265, DE-A-44 46 907 and EP-A-842 699. Raney copper can be prepared in a manner known per se by treating copper-aluminum alloys with alkali metal hydroxides. A Raney catalyst suitable for use in the process according to the invention is obtainable, for example, by preparation of a mixture of at least one copper-containing catalyst alloy and at least one binder, the catalyst alloy comprising copper and, if appropriate, at least one further catalytically active catalyst metal and a leachable alloy component, if appropriate with addition of moistening agents and/or additives, such as molding assistants, lubricants, plasticizers and/or pore formers, homogenization of this mixture and molding to give the desired molding, calcination of the molding and activation of the catalyst precursor thus obtained, by partial or complete leaching out of the leachable alloy component and, if appropriate, final washing of the prepared catalyst.

A further special embodiment of catalysts which are particularly advantageously used in the process according to the invention comprises catalysts which comprise copper in oxidic form and, if appropriate, additionally in elemental form. The hydrogenation catalyst used in step b) then preferably comprises at least 23% by weight, particularly preferably at least 35% by weight, of copper in oxidic and/or elemental form, based on the total weight of the catalyst.

A frequently used process for the preparation of such catalysts comprises the impregnation of support materials with solutions of the catalyst components, which are then converted into the catalytically active state by thermal treatment, decomposition or reduction.

A further suitable process for the preparation of catalysts comprises the precipitation of a catalyst component or the coprecipitation of two or more catalyst components. Thus, a copper compound, optionally at least one further metal compound and/or an additive are precipitated and subjected to subsequent drying, calcination and shaping to produce a shaped catalyst body. The precipitation can be performed in the presence of a support material. Suitable starting materials for the precipitation are metal salts and metal complexes. As copper compound for the precipitation it is in principle known to use all Cu(I) and/or Cu(II) salts which are soluble in the solvents used for application to the support, for example nitrates, carbonates, acetates, oxalates or ammonium complexes. Particular preference is given to using copper nitrate.

The catalytically active component of the catalyst may further comprise, apart from a copper compound, other elements as additive components, e.g. metals, nonmetals and their compounds. These preferably include a metal of groups 4 to 15 and the lanthanides. These preferably include metals as La, Ti, Zr, Cu, Mo, W, Mn, Re, Co, Ni, Cu, Ag, Au, Zn, Sn, Pb, As, Sb and Bi. Preferably, an aqueous medium is used for the precipitation.

Suitable aqueous media are substances or mixtures which are liquid under the process conditions and contain at least 10% by weight, preferably at least 30% by weight and in particular at least 50% by weight, of water. The part other than water is preferably selected from among inorganic or organic substances which are at least partially soluble in water or at least partially miscible with water. For example, the substances other than water are selected from among organic solvents, $C_1$-$C_{22}$-alkanols, in particular methanol, ethanol, n-propanol, isopropanol, n-butanol, sec-butanol, tert-butanol, pentanoles and hexanoles, $C_4$-$C_8$-cycloalkyl ethers, such as tetrahydrofurans, pyrans, dioxanes and trioxanes, $C_1$-$C_{12}$-dialkyl ethers, such as dimethyl ether, dibutyl ether and methyl butyl ether. The aqueous medium preferably contains less than 40%, in particular less than 30% and particularly preferably less than 20%, of organic solvent. In preferred embodiments of the process of the present invention, the aqueous medium is essentially free of organic solvents.

Precipitation can be induced by known methods, e.g. cooling a saturated solution, adding a precipitating agent, etc. Suitable precipitating agents are e.g. acids, bases, reducing agents, etc.

Precipitation can be induced by addition of an acid or a base to the aqueous medium containing the copper compound and optionally further compounds. Suitable acids are mineral acids, like HCl, $H_2SO_4$ and $H_3PO_4$. The base is preferably selected from among metal oxides, metal hydroxides, in particular alkali metal hydroxides, such as sodium hydroxide and potassium hydroxide, metal carbonates, in particular alkali metal and alkaline earth metal carbonates, e.g. lithium carbonate, sodium carbonate, potassium carbonate, magnesium carbonate and calcium carbonate, nitrogen bases, in particular ammonia, primary, secondary and tertiary amines.

Examples of suitable reducing agents are carboxylic acids, such as formic acid, citric acid, lactic acid, tartaric acid and in particular the salts of carboxylic acids, preferably the alkali metal, alkaline earth metal, ammonium and $C_1$-$C_{10}$-alkylammonium salts, phosphorus or hypophosphorus acid, the salts of phosphorus or hypophosphorus acid, in particular the alkali metal or alkaline earth metal salts, $C_1C_{10}$-alkanols, such as methanol, ethanol and isopropanol, sugars, such as aldoses and ketoses in the form of monosaccharides, disaccharides and oligosaccharides, in particular glucose, fructose and lactose, aldehydes, such as formaldehyde, boron-hydrogen compounds, such as boron hydrides, boranes, metal boranates and borane complexes, e.g. diborane, sodium borohydride and aminoboranes, in particular trimethylaminoborane, hydrazine and alkylhydrazines, such as methylhydrazine, hydrogendithionites and dithionites, in particular sodium and potassium hydrogendithionites, sodium, potassium and zinc dithionites, hydrogensulfites and sulfites, in particular sodium and potassium hydrogensulfites, sodium, potassium and calcium sulfites, hydroxylamine and urea, and also mixtures thereof.

For example, catalysts which comprise nickel and copper, in addition to other metals, as active constituents on a silica support are suitable for the hydrogenation. Such catalysts are described, for example, in DE-A 26 28 987. The active material of these catalysts comprises in particular from 40 to 80% by weight of nickel, from 10 to 50% by weight of copper and from 2% to 10% by weight of manganese.

EP-A-0 434 062 describes hydrogenation catalysts which are obtainable by reduction of a precursor comprising oxides of copper, of aluminum and at least of one further metal selected from magnesium, zinc, titanium, zirconium, tin, nickel and cobalt.

The hydrogenation catalysts which are described in DE 102 18 849 and comprise from 0.1 to 10% by weight of chromium, calculated as $Cr_2O_3$, from 0.1 to 10% by weight of calcium, calculated as $CaO_x$ and from 5 to 20% by weight of copper, calculated as CuO, deposited on a silica support material and based in each case on the total weight of the calcined catalyst, are also suitable.

DE-A-40 21 230 discloses copper/zirconium oxide catalysts, the ratio of copper atoms to zirconium atoms, expressed as a weight ratio, being from 1:9 to 9:1.

DE-A-4 028 295 describes copper/manganese hydrogenation catalysts.

EP-A-552463 describes hydrogenation catalysts in a first embodiment, the oxidic form substantially corresponding to the composition $Cu_aAl_bZr_cMn_dO_x$, the following relationships being applicable: a>0; b>0; c>/=0; d>0; a>b/2; b>a/4; a>c; a>d;

and x is the number of oxygen ions which is required for preserving the electroneutrality per formula unit. According to a further embodiment, the catalyst according to the invention comprises a smaller proportion of alumina. The catalyst according to this embodiment substantially corresponds to the composition $Cu_aAl_bZr_cMn_dO_x$, the following relationships being applicable: a>0; b=a/40 to a/4; c>/=0; d>0; a>c; a=0.5d to 0.95d and x is the number of oxygen ions which is required for preserving the electroneutrality per formula unit.

WO 2006/005505 discloses moulded catalyst bodies that are particularly advantageous for use in the process according to the invention. Those catalysts can be produced by a process in which (i) an oxidic material comprising copper oxide, aluminum oxide and at least one of the oxides of lanthanum, tungsten, molybdenum, titanium or zirconium, with preference being given to the oxides of lanthanum and/or tungsten, is made available, (ii) pulverulent metallic copper, copper flakes, pulverulent cement or a mixture thereof or a mixture thereof with graphite can be added to the oxidic material, and (iii) the mixture resulting from (ii) is shaped to form a catalyst pellet or a catalyst extrudate having a diameter d and/or a height h of <2.5 mm, catalyst spheres having a diameter d of <2.5 mm or catalyst honeycombs having a cell diameter $r_z$ of <2.5 mm.

Among the oxides of lanthanum, tungsten, molybdenum, titanium or zirconium, lanthanum oxide is preferred. The composition of the oxidic material is generally such that the proportion of copper oxide is in the range from 40 to 90% by weight, the proportion of oxides of lanthanum, tungsten, molybdenum, titanium or zirconium is in the range from 0 to 50% by weight and the proportion of aluminum oxide is up to 50% by weight, in each case based on the total weight of the abovementioned oxidic constituents, with these three oxides together making up at least 80% by weight of the oxidic material after calcination and cement not being included as part of the oxidic material in the above sense.

In a preferred embodiment, the oxidic material comprises
(a) copper oxide in a proportion in the range $50 \leq x \leq 80\%$ by weight, preferably $55 \leq x \leq 75\%$ by weight, (b) aluminum oxide in a proportion in the range $15 \leq y \leq 35\%$ by weight, preferably $20 \leq y \leq 30\%$ by weight, and (c) at least one of the oxides of lanthanum, tungsten, molybdenum, titanium or zirconium, preferably of lanthanum and/or tungsten, in a proportion in the range $2 \leq z \leq 20\%$ by weight, preferably $3 \leq z \leq 15\%$ by weight, in each case based on the total weight of the oxidic material after calcination, where $80 \leq x+y+z \leq 100$, in particular $95 \leq x+y+z \leq 100$.

Preferred catalysts comprise the following metals in oxidic form, reduced form (elemental form) or a combination thereof. Metals that are stable in more than one oxidation state can be employed entirely in one of the oxidation states or a combination of different oxidation states:

Cu
Cu, Ti
Cu, Zr
Cu, Mn
Cu, Al
Cu, Ni, Mn
Cu, Al, at least one further metal selected from La, W, Mo, Mn, Zn, Ti, Zr, Sn, Ni, Co
Cu, Zn, Zr
Cu, Cr, Ca
Cu, Cr, C
Cu, Al, Mn, optionally Zr Especially preferred catalysts comprise the following metals:

Cu
Cu, Ti
Cu, Al
Cu, Al, La
Cu, Al, Zn
Cu, Zn, Zr
Cu, Al, Mn
Cu, Cr, C

Virtually all support materials of the prior art, as advantageously used in the preparation of supported catalysts, for example, $SiO_2$ (quartz), porcelain, magnesium oxide, tin dioxide, silicon carbide, $TiO_2$ (rutile, anatas), $ZrO_2$, $Al_2O_3$ (alumina), aluminum silicate, steatite (magnesium silicate), zirconium silicate, cerium silicate or mixtures of these support materials, may be used as inert support material for the catalysts according to the invention. Preferred support materials are alumina and silica. Silica materials of different origin and preparation, for example pyrogenically produced silicas or silicas produced by a wet chemical method, such as silica gels, aero gels or precipitated silicas, can be used as silica support material for the catalyst preparation (for the preparation of various $SiO_2$ starting materials cf.: W. Büchner; R. Schliebs; G. Winter; K. H. Büchel: Industrielle Anorganische Chemie; $2^{nd}$ edition, pages 532-533, VCH Verlagsgesellschaft, Weinheim 1986).

The catalysts may be present in the form of a geometric body, e.g. in form of spheres, rings, cylinders, cubes, cuboids or other geometric bodies. Unsupported catalysts can be shaped by customary processes, e.g. by extruding, tabletting, etc. The form of supported catalysts is usually determined by the shape of the support. In an alternative, the support can be subjected to a shaping process prior to or after application of the catalytically active compound(s) or a precursor thereof. The catalysts can be employed e.g. in the form of pressed cylinders, tablets, lozenges, wagon wheels, rings, stars or extrudates, such as solid extrudates, polylobal extrudates (e.g. trilobal), hollow extrudates and honeycomb bodies.

The catalyst particles generally have a mean value of the (largest) diameter of from 0.5 to 20 mm, preferably from 1 to 10 mm. These include, for example, catalysts in the form of tablets, for example having a diameter of from 1 to 7 mm, preferably 2 to 6 mm, and a height of from 3 to 5 mm, rings having, for example an external diameter of from 4 to 7 mm, preferably 5 to 7 mm, a height of from 4 to 7 mm, preferably 2 to 5 mm, and a hole diameter of from 2 to 3 mm, or strands of different lengths having a diameter of, for example, from 1.0 to 5 mm. Such shapes can be obtained in a manner known per se, by tabletting, extrusion molding or extrusion. For this purpose, conventional adjuvants, for example lubricants, such as graphite, polyethylene oxide, cellulose or fatty acids (such as stearic acid), and/or molding assistants and reinforcing agents, such as fibers of glass, asbestos or silicon carbide can be added to the catalyst material.

A special embodiment of supported catalysts comprises coated catalysts. Coated catalysts are also preferably suitable for the process according to the invention. Coated catalysts comprise a catalytic material applied in the form of a coat to a support. They may be present in the form of spheres, rings, cylinders, cubes, cuboids or other geometrical bodies. Regardless of the type and composition of the catalytically active material, coated catalyst particles can be provided in principle by bringing the support into contact with a liquid binder and the catalytically active material, applying a layer of the material to the support and then, if appropriate, partially removing the binder. In order to provide the catalyst particles, the catalytically active material is applied already in its prepared catalytically active form, for example as calcined mixed oxide. Suitable processes for the preparation of coated catalysts are described, for example, in DE-A-29 09 671 and in EP-A-714 700. According to the last-mentioned process, the support is first moistened with the liquid binder, a layer of active catalyst material is then bonded to the surface of the moistened support body by bringing into contact with dry, finely divided, active catalyst material, and, if appropriate, the liquid binder is then partly removed. In a special embodiment, the steps of moistening of the support, bringing into contact with the catalyst material and removal of the liquid binder are repeated once or several times until the desired layer thickness of the coated catalyst is reached.

A further special embodiment of supported catalysts comprises catalysts prepared by impregnation methods. For this purpose, the catalytically active catalyst components or precursor compounds thereof can be applied to the support material. In general, aqueous salt solutions of the components, for example aqueous solutions of their halides, sulfates, nitrates, etc. are applied for impregnating the support material. The copper component can also be applied, for example, in the form of an aqueous solution of its amine complex salts, for example as $[Cu(NH_3)_4]SO_4$ or as $[Cu(NH_3)_4](NO_3)_2$ solution, if appropriate in the presence of sodium carbonate, to the support material. Of course, copper-amine complexes other than those mentioned by way of example can also be used with the same success for the catalyst preparation.

The impregnation of the support material with the precursor compounds of the catalytically active components can be effected in principle in one stage or in a plurality of stages. The impregnation can be carried out in conventional impregnation apparatuses, for example impregnation drums. After drying and/or calcination, the prepared catalyst is then obtained. The drying of the impregnated catalyst moldings can be effected continuously or batchwise, for example in belt or tray furnaces. The drying can be effected at atmospheric pressure or reduced pressure. Furthermore the drying can be effected in a gas stream, for example in an air stream or a nitrogen stream. Depending on the pressure applied, the drying is generally carried out at temperatures of from 50 to 200° C., preferably from 80 to 150° C. The calcination of the catalyst, dried beforehand if appropriate is effected in general at temperatures of from 200 to 800° C., preferably from 500 to 700° C. The calcination, like the drying, can be carried out continuously or batchwise, for example in belt or tray furnaces. The calcination can be effected at atmospheric pressure or reduced pressure and/or in a gas stream, for example in an air stream or hydrogen stream. A pretreatment with hydrogen or gases comprising hydrogen, in general under conditions which correspond to the hydrogenation conditions, serves for preliminary reduction/activation of the hydrogenation catalyst. However, the catalyst can also be reduced in situ under the conditions specified in the case of the hydrogenation, preferably under pressure (for example at a hydrogen pressure of from about 100 to 325 bar).

In the hydrogenation, the glycerol and the resulting 1,2-propanediol are preferably present in the liquid phase.

The catalysts may be arranged, for example, in a fixed bed or may be used as a suspension. The hydrogenation can accordingly be carried out, for example, by the trickle-bed procedure or the liquid-phase procedure. For the liquid-phase hydrogenation, the catalysts are preferably used in finely divided form, for example as powder, in suspension. In the hydrogenation in the trickle phase, the catalysts are used as moldings, as described above, for example in the form of pressed cylinders, tablets, lozenges, wagon wheels, rings, stars or extrudates, such as solid extrudates, polylobal extrudates, hollow extrudates and honeycomb bodies. Excess hydrogen is preferably circulated, it being possible for a small part to be discharged as waste gas for removing inert materials. It is possible to use one reactor or a plurality of reactors which can be connected in series or parallel to one another.

The temperature in the hydrogenation in step b) is preferably from 150 to 300° C., in particular from 175 to 250° C.

The reaction pressure in step b) is preferably from 140 bar to 250 bar.

The molar ratio of hydrogen to glycerol is preferably from 2:1 to 500:1, preferably from 3:1 to 100:1.

The catalyst space velocity in the continuous procedure is preferably from 0.1 to 1, more preferably from 0.2 to 0.6, and in particular from 0.3 to 0.6, kg of glycerol to be hydrogenated per kg (catalyst) per h.

The conversion, based on glycerol, is preferably at least 90%, in particular at least 95%. The selectivity, based on 1,2-propanediol is preferably at least 85%, particularly preferably at least 90%, in the process according to the invention. Often, even higher selectivities of up to 95% or more can be achieved.

The hydrogenation is expediently carried out continuously. The hydrogenation discharge substantially comprises 1,2-propanediol. Further constituents are, inter alia, methanol, ethanol, n-propanol, isopropanol, 1,3-propanediol, glycerol, ethylene glycol and water. The hydrogenation discharge can then be worked up by conventional methods known to the person skilled in the art. For example, thermal working-up, preferably distillation, adsorption, ion exchange, a membrane separation method, crystallization or extraction or a combination of two or more of these methods can be used. Preferred is a working-up by distillation. This can in principle be effected by conventional distillation methods known to the person skilled in the art. Suitable apparatuses for the distillative working-up comprise distillation columns, such as tray columns, which may be equipped with caps, sieve plates, sieve trays, stacked packings, dumped packings, valves, side take-offs, etc. evaporators, such as thin-film evaporators, falling-film evaporators, forced-circulation evaporators, Sambay evaporators, etc., and combinations thereof. Glycerol still present in the hydrogenation discharge can be recycled to the hydrogenation stage, if appropriate after being separated off by distillation.

The invention is explained in more detail with reference to the following, non-limiting examples.

EXAMPLES

Glycerol of the pharmaceutical glycerol and pure glycerol qualities from Biodiesel Schwarzheide GmbH was used as feedstock for the experiments for catalyst screening. Table 1 shows the analytical data of the glycerol used.

TABLE 1

| Glycerol quality | Water [%] | pH [pH] | chloride [ppm] | Glycerol content [%] |
|---|---|---|---|---|
| Pure | 0.1 | 7 | 2 | 97-98 |
| Pharmaceutical | 0.141 | 7 | 1.4 | 99.8 |

The analysis of the feedstock glycerol and of the reaction discharge is effected by gas chromatography (data in GC % by area).

| | |
|---|---|
| Apparatus: | HP 5890-2 with sampler |
| Range: | 2 |
| Column: | 30 m DBWax; film thickness: 0.25 μm |
| Sample volume: | 1 μl |
| Carrier gas: | Helium |
| Fluid rate: | 100 ml/min |
| Injector temperature: | 240° C. |
| Detector: | FID (Flame ionization detector) |
| Detector temperature: | 250° C. |
| Temperature program: | 5 min at 40° C., 10° C./min to 240° C., 15 min at 240° C. |
| | Total run time 45 min |

Copper-containing catalysts of different compositions were tested (cf. table 2).

TABLE 2

Overview of the catalysts tested

| Catalyst | Composition |
|---|---|
| A | 67% CuO; 5% $La_2O_3$; $Al_2O_3$ (ad 100%) + 15% Cu |
| B | 40% CuO; 40% ZnO; 20% $Al_2O_3$ |
| C* | 40% CuO; 40% ZnO; 20% $Al_2O_3$ |
| D | 61% CuO; 39% $Al_2O_3$ |
| E | 70% CuO; 24.5% ZnO; 5.5% $Al_2O_3$ |
| F | 55% CuO/$Al_2O_3$ |
| G | 16% CuO/64% $Al_2O_3$/20% ZnO |
| H | 100% Cu (Raney-Cu**) |
| I | 40% Cu/$TiO_2$ |
| J | 70% CuO/20% ZnO/10% $ZrO_2$ |
| K | 60% CuO/30% $Al_2O_3$/10% $MnO_3$ |
| L | 66-77% CuO/21-32% Cu-Chromit/2% Graphit |

*as for B, but higher calcination temperature (from 400 to 500° C.)
**from Aldrich The catalysts were activated for 10 h at a temperature of 200° C. and a hydrogen pressure of 50 bar before the reaction.

General Method for Carrying Out Catalyst Tests Batchwise.

Pharmaceutical glycerol having a water content of 20% was used. The catalyst was initially taken in a 0.3 l mini autoclave and the autoclave was closed and was tested for leaks with 200 bar $N_2$ at room temperature. Catalyst extrudates were used in the form of moldings, and the extrudates were comminuted beforehand for the preparation of catalyst suspensions.

Thereafter, the autoclave was depressurized and the activation of the catalyst carried out. For this purpose, 50 bar $H_2$ was forced in at room temperature, heating was then effected to an internal temperature of 200° C. and the temperature was maintained for about 10 h without stirring. After cooling to 30° C. and subsequent inertization with $N_2$ the autoclave was evacuated and the reaction solution was aspirated.

For the reaction of the glycerol, 50 bar $H_2$ was forced in at room temperature and the reaction mixture was heated to 215° C. with stirring (speed from 700 to 1000 rpm). The pressure resulting in the autoclave was supplemented with $H_2$ to the desired final pressure of 200 bar. Hydrogen consumed in the reaction was replenished. The run time of the experiments was 10 hours. After the end of the run time of the experiment, the autoclave was cooled to room temperature and depressurized. The analysis of the samples and discharges was effected by means of gas chromatography by integration of the areas of the peaks (% by area). The results are shown in table 3.

TABLE 3

Comparison of the catalyst in the fixed bed and suspension procedures

| Ex. No. | Catalyst | Catalyst form | Amount of catalyst [g] | Conversion [%] | Selectivity [%] | Yield [%] |
|---|---|---|---|---|---|---|
| 1 | A | Suspension | 20.0 | 97.6 | 95.3 | 93.0 |
| 2 | B | Extrudates 5 × 3 | 10.0 | 91.5 | 91.2 | 83.5 |
| 3 | C | Extrudates 5 × 3 | 18.3 | 100.0 | 87.8 | 87.8 |
| 4 | D | Suspension | 20.0 | 97.2 | 93.6 | 91.0 |
| 5 | E | Extrudates 5 × 5 | 10.0 | 99.1 | 88.8 | 88.0 |
| 6 | F | Suspension | 20.0 | 96.8 | 94.4 | 91.3 |
| 7 | G | Suspension | 10.0 | 92.3 | 92.5 | 85.4 |
| 8 | H | Suspension | 10.0 | 99.6 | 96.1 | 95.8 |
| 9 | J | tablets | 18.0 | 92.7 | 96.6 | 89.6 |
| 10 | K | tablets | 18.0 | 79.6 | 94.5 | 75.2 |
| 11 | L | tablets | 18.0 | 74.5 | 96.8 | 72.1 |

General Method for the Continuous Hydrogenation Using Fixed-Bed Catalysts

Pharmaceutical glycerol having a water content of 10% was used. The experiments were carried out in a continuously operated laboratory apparatus at from 200 to 240 bar. The experimental series 9 to 11 were operated for simulating the main reactor with liquid circulation in the liquid-phase procedure. In each case 70 ml of the catalysts were used.

The structure of the unit and the process description are described below:

The unit consists of a 75 ml tubular reactor R1 (internal Ø=12 mm, L=800 mm) having three liquid-heated heating zones, which is operated by the liquid-phase procedure. If required a liquid circulation which is operated with flow control (Danfoss) via an HPLC pump can be connected. All parts of the unit are made from metal and designed for an operating pressure of up to 250 bar.

The glycerol solution (aqueous, 90% strength) is metered continuously, regulated by a balance, into the reactor R1 and is reacted under defined conditions (pressure, temperature, catalyst space velocity) with hydrogen to give the desired product. The hydrogen is supplied from 50 l steel cylinders which are compressed to the required pressure by means of a compressed air-operated compressor. The desired reaction pressure is established via pressure control (P2) in the waste gas stream, and the required amount of hydrogen is fed into the reactor R1 with flow control via a mass flow meter (Hi-Tec). The liquid reactor discharge is discharged with level control (container B2) via an HPLC pump and collected in the discharge container (B5). The gaseous reactor discharge is passed via a buffer vessel (B4) and depressurized by means of a pressure-controlled (P2) Recco valve.

In experimental series 15, the reactions were continued in a modified unit (main reactor with liquid circulation in the trickle-bed procedure, downstream reactor without liquid circulation in the liquid-phase procedure). In all experiments, the catalyst was stable, no catalyst loss occurred as a result of so-called "leaching".

TABLE 4

Results of the continuous experiments (best setting from each experimental series)

| Expt. No. | Catalyst | Run time [h] | Temp. [° C.] | Pressure [bar] | Feed [g/h] | Cat. space vel. [kg/l · h] | LR g/h | pH Discharge | Glycerol conversion | Yield | Selectivity |
|---|---|---|---|---|---|---|---|---|---|---|---|
| 12 | I | 230 | 217 | 200 | 31.1 | 0.4 | 155 | 5.5 | 81 | 81 | 99 |
| 13 | I | 153 | 220 | 240 | 31.1 | 0.4 | 0 | 6 | 96 | 94 | 98 |
| 14 | A | 287 | 200 | 200 | 23.3 | 0.3 | 300 | 6 | 88 | 82 | 92 |
| 15 | B | 253 | 170-190 | 200 | 44.4 | 0.4 | 1800 | 6-7 | 100 | 98.5 | 98.5 |

LR = liquid recycling (circulation) from the reactor exit to the reactor entrance

We claim:

1. A process for preparing 1,2-propanediol, comprising
a) providing a glycerol-containing stream; and
b) hydrogenating said glycerol-containing stream in the presence of a heterogeneous catalyst which comprises copper at a temperature in the range of from 100° C. to 320° C. and at a pressure in the range of from 100 bar to 325 bar;
wherein said glycerol-containing stream has a water content of 30% by weight or less.

2. The process of claim 1, wherein said glycerol-containing stream is obtained from the preparation of alkyl esters of higher fatty acids by transesterification of fatty acid triglycerides.

3. The process of claim 1, wherein said glycerol-containing stream has a water content of 20% by weight or less.

4. The process of claim 1, wherein said glycerol-containing stream is substantially anhydrous.

5. The process of claim 1, wherein said glycerol-containing stream is worked-up via at least one work-up process selected from the group consisting of thermal working-up, adsorption, ion exchange, membrane separation, crystallization, extraction, and combinations thereof.

6. The process of claim 1, wherein the water content of said glycerol-containing stream is reduced and/or components which adversely affect catalytic hydrogenation are removed from said glycerol-containing stream via distillation.

7. The process of claim 1, wherein said glycerol-containing stream is subjected to catalytic desulfurization prior to step b).

8. The process of claim 7, wherein said catalytic desulfurization is performed in the presence of hydrogen.

9. The process of claim 7, wherein said sulfur-containing compounds comprise sulfur-containing aromatic compounds.

10. The process of claim 1, wherein said glycerol-containing stream is contacted with at least one adsorbent for removing components which adversely affect catalytic hydrogenation.

11. The process according to claim 1, wherein said adsorbent comprises at least one component capable of use as a hydrogenation catalyst.

12. The process according to claim 1, wherein said glycerol-containing stream is provided by:
a1) providing a biogenic fat-and/or oil-containing starting mixture comprising fatty acid triglycerides and free fatty acids;
a2) transesterifying said fatty acid triglycerides with at least one $C_1$-$C_9$-monoalcohol and, optionally, esterifying said free fatty acids, to form an esterification mixture;
a3) separating said esterification mixture so as to obtain at least one fraction enriched with $C_1$-$C_9$-monoalkyl esters and at least one fraction enriched with glycerol liberated in the transesterification of a2),
a4) optionally, purifying said at least one fraction enriched with glycerol.

13. The process according to claim 1, wherein said heterogenous catalyst comprises a Raney catalyst.

14. The process of claim 1, wherein said heterogenous catalyst comprises at least 23% by weight of copper, in oxidic and/or elemental form, based on the total weight of the catalyst.

15. The process of claim 1, wherein said heterogenous catalyst comprises at least 35% by weight of copper, in oxidic and/or elemental form, based on the total weight of the catalyst.

16. The process of claim 1, wherein said heterogenous catalyst comprises metals or mixtures of metals selected from the group consisting of Cu; Cu and Ti; Cu and Zr; Cu and Mn; Cu and Al; Cu, Ni, and Mn; Cu, Al, and at least one further metal selected from the group consisting of La, W, Mo, Mn, Zn, Ti, Zr, Sn, Ni, and Co; Cu, Zn, and Zr; Cu, Cr, and Ca; Cu, Cr, and C; and Cu, Al, Mn, and optionally Zr; wherein each metal is present in oxidic form, elemental form, or a combination thereof.

* * * * *